(12) United States Patent
Axelrod et al.

(10) Patent No.: US 11,771,049 B2
(45) Date of Patent: Oct. 3, 2023

(54) DISPOSABLE ABSORBENT PAD AND METHOD OF DISPOSING OF THE SAME

(71) Applicant: FOUR PAWS PRODUCTS, LTD., Neptune City, NJ (US)

(72) Inventors: Glen S. Axelrod, Colts Neck, NJ (US); Ajay Gajria, Maharashtra (IN); Diana M. Echeverri, Beachwood, NJ (US)

(73) Assignee: FOUR PAWS PRODUCTS, LTD, Neptune City, NJ (US)

( * ) Notice: Subject to any disclaimer, the term of this patent is extended or adjusted under 35 U.S.C. 154(b) by 272 days.

(21) Appl. No.: 16/824,770

(22) Filed: Mar. 20, 2020

(65) Prior Publication Data

US 2020/0296918 A1    Sep. 24, 2020

Related U.S. Application Data

(60) Provisional application No. 62/821,076, filed on Mar. 20, 2019.

(51) Int. Cl.
*A01K 1/01* (2006.01)
*A01K 1/015* (2006.01)
(Continued)

(52) U.S. Cl.
CPC .......... *A01K 1/0107* (2013.01); *A01K 1/0157* (2013.01); *A01K 23/005* (2013.01);
(Continued)

(58) Field of Classification Search
CPC .. A01K 1/0107; A01K 1/0157; A01K 23/005; A01K 1/01; A01K 1/0125;
(Continued)

(56) References Cited

U.S. PATENT DOCUMENTS 3,626,899 A * 12/1971 Spellman ............... A01K 15/02
119/169
3,626,900 A * 12/1971 Failla ................... A01K 1/0107
119/161
(Continued)

FOREIGN PATENT DOCUMENTS

EP    3178316    6/2017
GB    2425032    10/2006
(Continued)

OTHER PUBLICATIONS

First Office Action from related Chinese Appln. No. 202080019626.0, dated Mar. 3, 2022. English translation attached.
(Continued)

*Primary Examiner* — Trinh T Nguyen
(74) *Attorney, Agent, or Firm* — Grossman, Tucker, Perreault & Pfleger, PLLC

(57) ABSTRACT

A method of disposing of an absorbent pad may include pivoting a flexible bag from a storage position to a use position such that at least a portion of the flexible bag extends from the absorbent pad, folding a left and right portion of the flexible bag towards a center portion of the flexible bag to form a stacked portion, rolling the stacked portion towards the flexible bag to form a roll, and disposing the roll within a cavity defined by one of an outer surface or an inner surface of the flexible bag.

18 Claims, 14 Drawing Sheets

(51) Int. Cl.
  *A01K 23/00* (2006.01)
  *B32B 27/32* (2006.01)
  *B32B 27/30* (2006.01)
  *B32B 27/10* (2006.01)
  *A61F 13/15* (2006.01)

(52) U.S. Cl.
  CPC ............ *B32B 27/10* (2013.01); *B32B 27/308* (2013.01); *B32B 27/32* (2013.01); *A61F 2013/15186* (2013.01); *B32B 2307/7265* (2013.01)

(58) Field of Classification Search
  CPC ......... A61F 2013/15186; A61F 13/551; B32B 27/10; B32B 2307/7265; B32B 5/24; B32B 5/30; B32B 5/00; B32B 27/12; B32B 29/02
  See application file for complete search history.

(56) References Cited

U.S. PATENT DOCUMENTS

| | | | | |
|---|---|---|---|---|
| 4,156,400 | A | * | 5/1979 | Migdal ................. E01H 1/1206 294/1.3 |
| 4,430,087 | A | | 2/1984 | Azpiri |
| 4,604,096 | A | | 8/1986 | Dean et al. |
| 4,756,273 | A | | 7/1988 | Yananton |
| 4,869,204 | A | * | 9/1989 | Yananton ............. A01K 1/0107 119/169 |
| 5,062,392 | A | * | 11/1991 | Lavash ................ A01K 1/0114 119/167 |
| 5,178,426 | A | * | 1/1993 | David .................. A01K 1/0107 294/1.3 |
| 5,549,945 | A | | 8/1996 | Lind |
| 5,850,798 | A | * | 12/1998 | Engel .................. A01K 1/0107 119/170 |
| 6,481,766 | B1 | | 11/2002 | May et al. |
| 7,249,570 | B1 | | 7/2007 | Roberson |
| 8,042,490 | B2 | * | 10/2011 | Takahashi ............ A01K 1/0107 119/169 |
| 9,283,126 | B2 | | 3/2016 | Amiri |
| 9,357,746 | B2 | * | 6/2016 | Miller .................. A01K 1/0125 |
| 2005/0109284 | A1 | * | 5/2005 | Heitman ............... A01K 1/0107 119/161 |
| 2006/0124068 | A1 | | 6/2006 | Matsuo et al. |
| 2006/0260559 | A1 | | 11/2006 | Fry et al. |
| 2007/0000446 | A1 | | 1/2007 | Dunn et al. |
| 2009/0194454 | A1 | | 8/2009 | Wong et al. |
| 2010/0307422 | A1 | | 12/2010 | Huck et al. |
| 2011/0139082 | A1 | | 6/2011 | Blagden |
| 2013/0068169 | A1 | | 3/2013 | Miller |
| 2017/0280671 | A1 | * | 10/2017 | Miller ...................... B32B 3/06 |
| 2018/0193002 | A1 | | 7/2018 | Langefels |

FOREIGN PATENT DOCUMENTS

| | | | |
|---|---|---|---|
| JP | 11164850 | | 6/1999 |
| JP | 2015119654 | | 7/2015 |
| JP | 2019000091 A | * | 1/2019 .......... A01K 1/0107 |
| KR | 10-2018-0017686 | | 2/2018 |
| KR | 20-2018-0003192 | | 11/2018 |
| WO | 2019/021286 | | 1/2019 |

OTHER PUBLICATIONS

International Search Report and Written Opinion from related PCT Appln. No. PCT/US2020/023751, dated Jun. 17, 2020.

Extended European Search Report from related EP Appln. No. 20774506.8, dated Nov. 8, 2022.

Office Action from related Australian Appln. No. 2020242072, dated Apr. 6, 2023.

* cited by examiner

18A

US 11,771,049 B2

1

DISPOSABLE ABSORBENT PAD AND METHOD OF DISPOSING OF THE SAME

CROSS-REFERENCE TO RELATED APPLICATIONS

The present application claims the benefit of U.S. Provisional Application Ser. No. 62/821,076 filed on Mar. 20, 2019, entitled Easy Disposal Absorbent Pad, which is fully incorporated herein by reference.

TECHNICAL FIELD

The present disclosure is generally related to an absorbent pad for pets that is combined with a moisture impermeable waste bag, which when in a soiled condition, can be easily disposed of by a user of the absorbent pad (e.g., a pet owner). More specifically, the combined absorbent pad/waste bag provides the opportunity to seal and reduce exposure of the absorbent pad after soiling and during disposal while also minimizing or avoiding contact of the pad to improve its sanitary use.

BACKGROUND

Pet owners may find it desirable to housetrain a new pet (e.g., a dog). The housetraining process may involve the pet owner teaching the pet to use a consistent location within the home to urinate. An absorbent pad may be placed at the location where the pet is taught to urinate such that urine is absorbed by the pad. As such, the urine may be more easily disposed of without harm to surfaces (e.g., a floor) within the home.

However, while absorbent pads have been widely utilized, the problem of odor control and relatively easy and convenient disposal remains an on-going problem. Accordingly, a need arises for the design of an absorbent pad that facilitates housetraining and which also provides the user a relatively easy procedure to facilitate disposal while also minimizing the potential contact of the user with a soiled and used pad.

BRIEF DESCRIPTION OF THE DRAWINGS

These and other features and advantages will be better understood by reading the following detailed description, taken together with the drawings, wherein.

DETAILED DESCRIPTION

Figure 1:
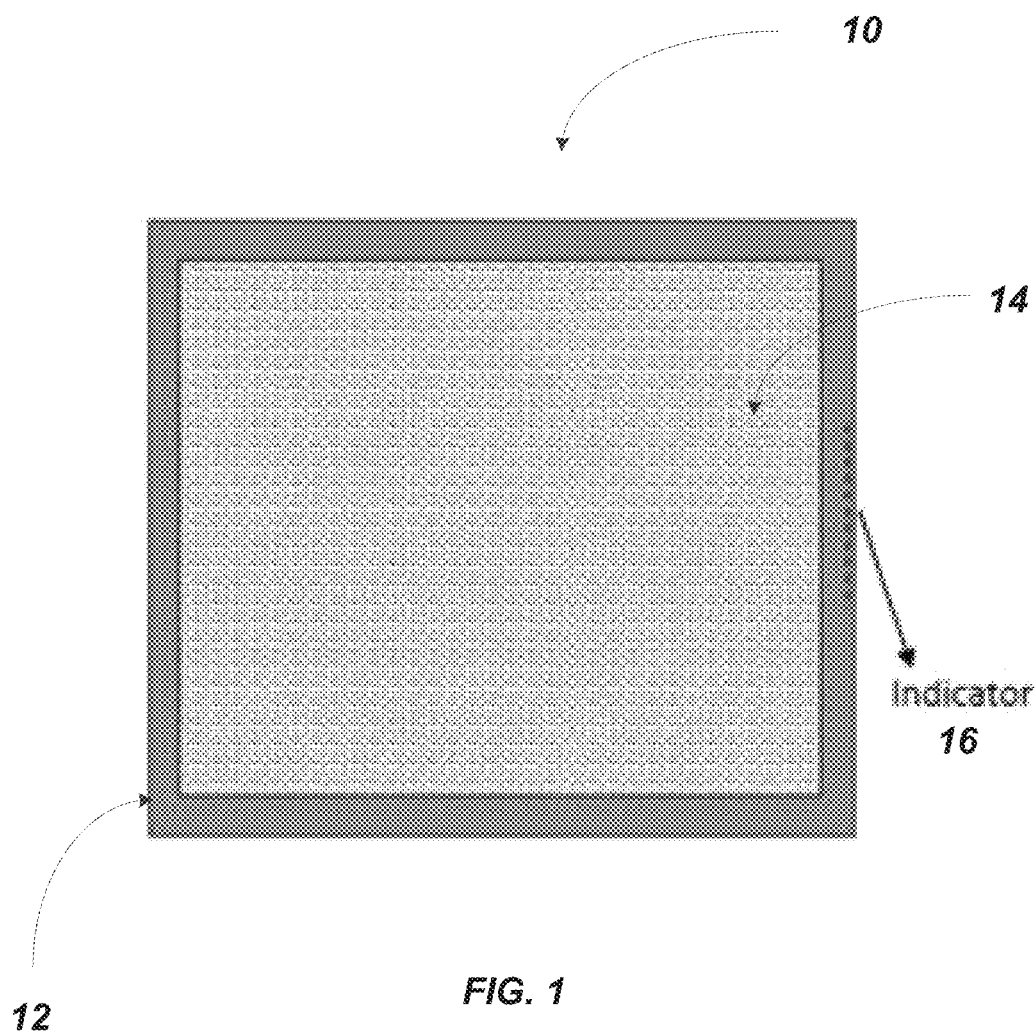
FIG. 1 is schematic front (or top) view of an absorbent pad, consistent with embodiments of the present disclosure.
Figure 2:
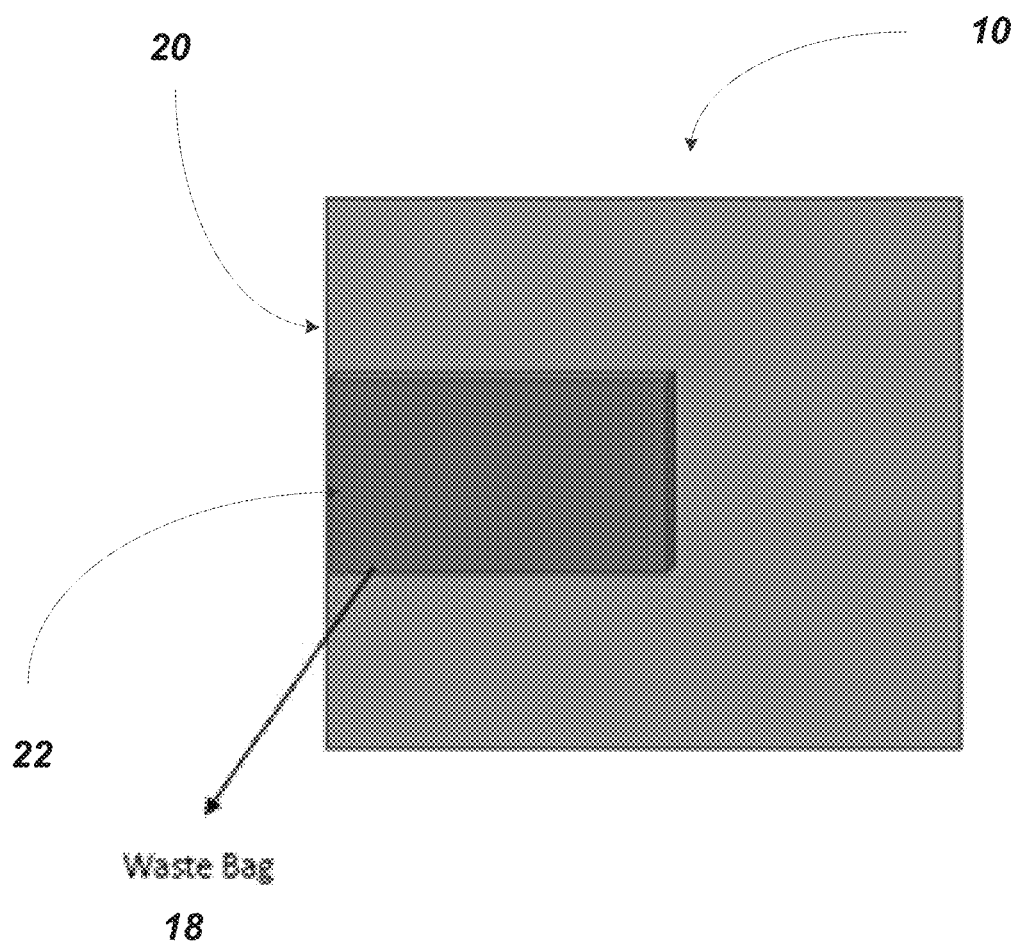
FIG. 2 is a schematic back (or bottom) view of the absorbent pad of FIG. 1 with a waste bag coupled thereto, consistent with embodiments of the present disclosure.

Attention is directed to FIG. 1 which provides a general perspective front (or top) view of the absorbent pad 10. As can be seen, the absorbent pad includes a border region 12 and an absorbent region 14. The pad also includes an indicator 16 which will visually inform the user that the opposing side of the pad includes an attached waste bag that will facilitate pad disposal. That is, with attention to FIG. 2, which provides a back (or bottom) view of the waste pad of FIG. 1, one can see that a waste bag (or flexible bag) 18 is attached to the absorbent pad for use by the user in disposing of the absorbent pad after use by an animal. The waste bag 18 is preferably attached along a border portion 20 of the absorbent pad 10 which may be preferably achieved by a lamination procedure where the bottom and sealed edge portion 22 of the waste bag is, for example, heat sealed to the absorbent pad 10. However, the waste bag 18 may be attached along the border portion 20 using any suitable form of attachment/coupling (e.g., one or more adhesives, one or more mechanical couplings, and/or any other form coupling). The waste bag is preferably formed from an impermeable film material, such as a polyolefin, more specifically a polyethylene type material. Reference to impermeable is reference to the feature that the film material does not transmit liquid, and in particular liquid animal waste, through its thickness.

Figure 3:
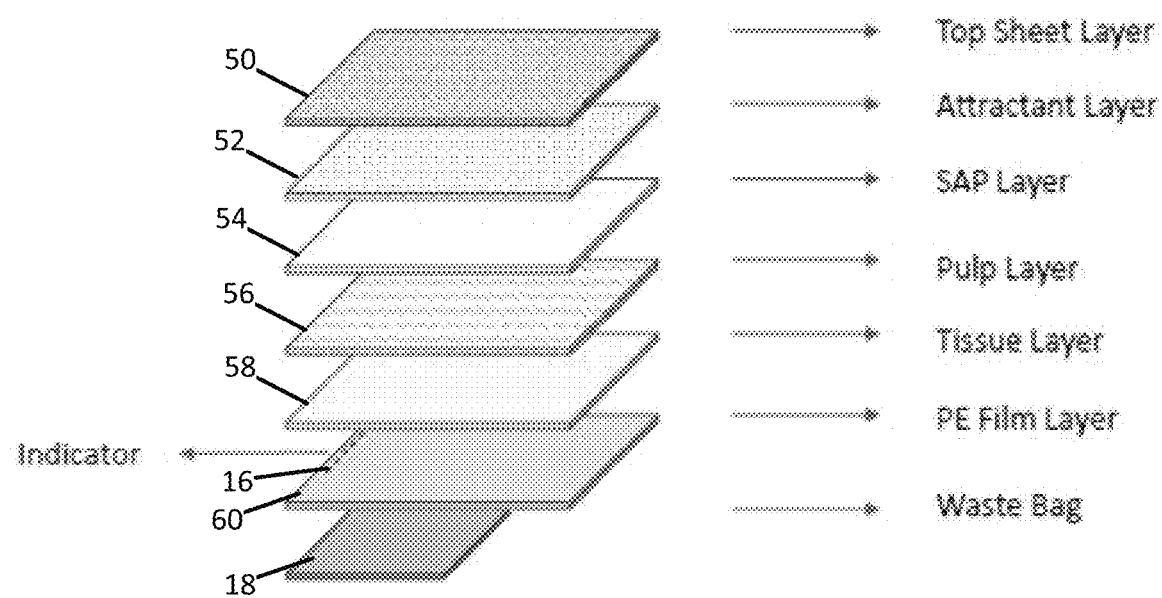
FIG. 3 is an exploded perspective view of the absorbent pad of FIG. 1, consistent with embodiments of the present disclosure.

The easily disposable absorbent pad 10 herein is also one that preferably includes multiple layers. As illustrated in FIG. 3, the absorbent pad preferably includes a top sheet layer 50 that is designed to be porous to liquid waste. This may then be followed by an attractant layer 52 which is designed to attract the animal via smell or other stimulant, and a super absorbent polymer (SAP) layer 54. It should also be appreciated that, optionally, additional layers may be present, such as an odor control layer or a scent layer which would mask or cover-up odors occurring after use.

The superabsorbent polymer may preferably have, for example, a retention absorbency in a range of 30 g/g to 45 g/g, an absorption capacity in a range of 55 g/g to 65 g/g (as measured in a 0.9% NaCl aqueous solution), an absorptive rate (e.g., a quantity of time to absorb 50, 100, or 150 milliliters of liquid such as a 0.9% NaCl aqueous solution) in a range of 15 seconds to 40 seconds, a moisture content in a range of 4% to 9%, a measure of residual acrylic acid monomers in a range of 15 parts-per-million (ppm) to 25 ppm, and a bulk density in a range of 0.6 g/ml to 0.85 g/ml. By way of further example, the superabsorbent polymer layer can include a superabsorbent polymer having a retention absorbency of 41 g/g, an absorption capacity of 60 g/g (as measured in a 0.9% NaCl aqueous solution), an absorptive rate of 29 seconds, a moisture content of 7.4%, a measure of residual acrylic acid monomers of 22 ppm, and a bulk density of 0.74 g/ml. By way of still further example, the superabsorbent polymer layer can include a superabsorbent polymer having a retention absorbency of 40 g/g, an absorption capacity of 60 g/g (as measured in a 0.9% NaCl aqueous solution), an absorptive rate of 30 seconds, a moisture content of 7.2%, a measure of residual acrylic acid monomers of 18 ppm, and a bulk density of 0.74 g/ml. Particle sizes of the superabsorbent polymer forming the superabsorbent polymer layer may measure less than 850 microns (μm). For example, between 80% and 90% of the particles may have a particle size measuring in a range of 180 μm to 500 μm.

As further seen in FIG. 3, there is a pulp layer 56. The pulp layer 56 may be formed by pulp fibers and/or pulp powder that is distributed within the layer as illustrated. This may then be followed by a tissue layer 58 which preferably comprises of tissue paper. This may then be followed by a film layer 60, such as a polyolefin type film layer, more specifically a polyethylene film layer. Such film layer is preferably one that is an impermeable film that prevents the flow of waste fluid from contacting the floor or other surface upon which the absorbent pad may be placed.

Figure 4:
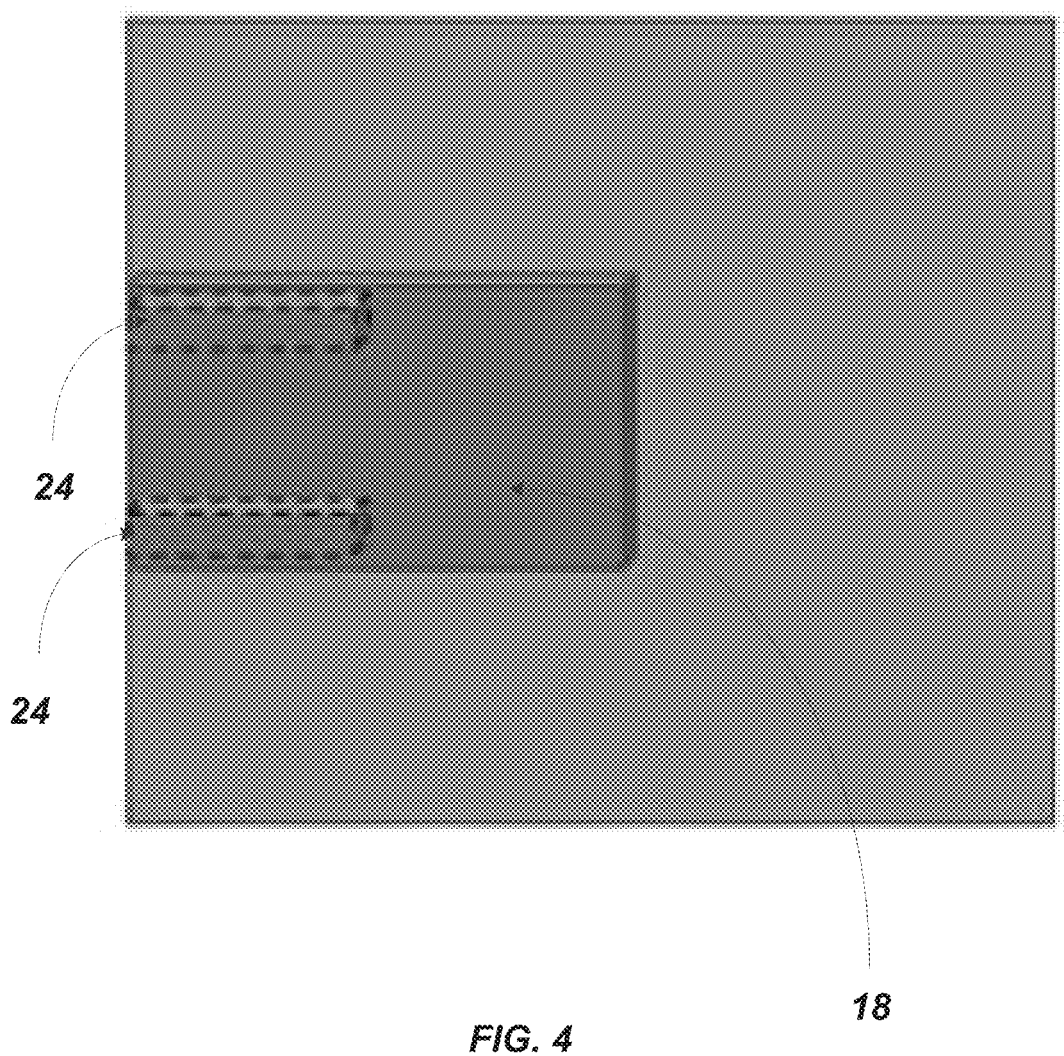
FIG. 4 shows a schematic bottom view of an example of the absorbent pad of FIG. 1, wherein the waste bag includes one or more handle portions, consistent with embodiments of the present disclosure.
Figure 4A:
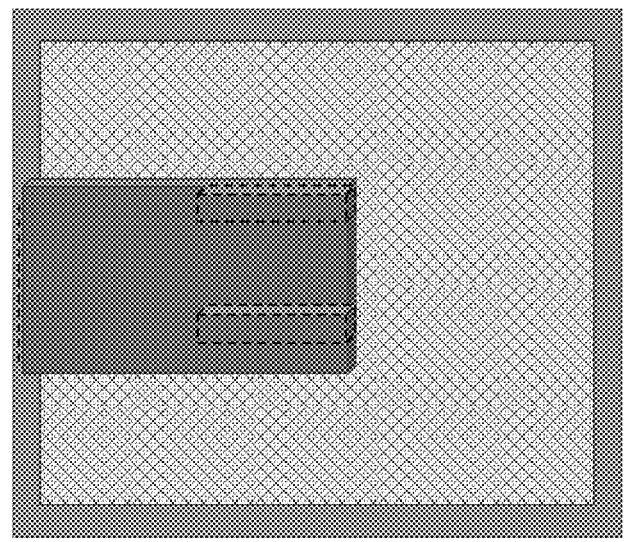
FIG. 4A shows a schematic bottom view of an example of the absorbent pad of FIG. 4, wherein the waste bag is coupled to the absorbent pad at an attachment region, consistent with embodiments of the present disclosure.
Figure 4B:
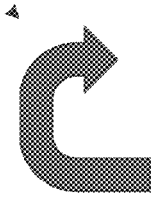
FIG. 4B shows a top view of the absorbent pad of FIG. 4A, consistent with embodiments of the present disclosure.
Figure 4B:
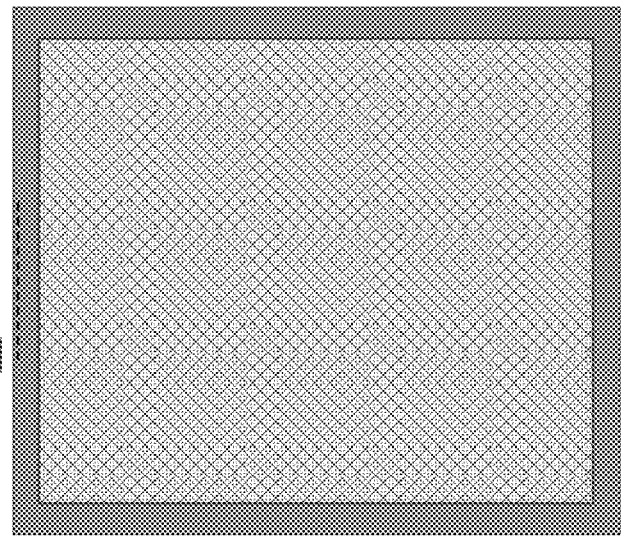
Figure 5:
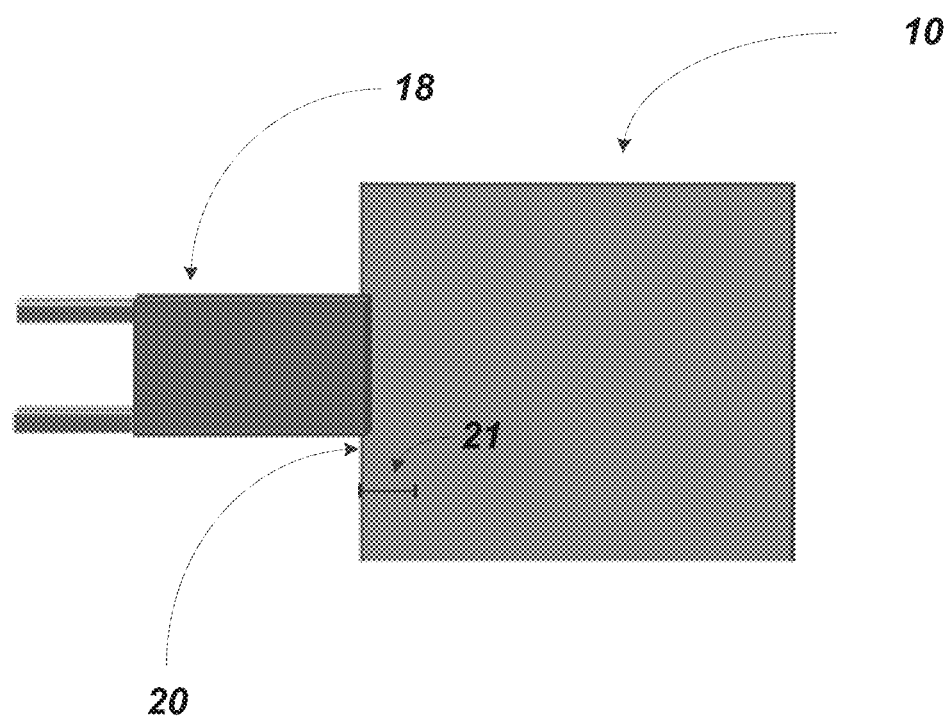
FIG. 5 shows a schematic bottom view of the absorbent pad of FIG. 4, wherein the waste bag is in a use position, consistent with embodiments of the present disclosure.

With attention to FIG. 4, the waste bag 18 preferably includes one or more handle portions 24 (two are illustrated in draft) that can be contained inside the waste bag and utilized when the user disposes of the absorbent pad. The waste bag can be attached along the border portion 20 of the absorbent pad either on the back of the pad (see FIG. 6 herein) or to the front of the pad as shown in FIG. 4A. If attached to the front of the absorbent pad, the waste bag is configured and can be made such that it can pivot about the border portion 20 of the absorbent pad and be placed under the absorbent pad, as shown generally by arrow 18A. FIG. 5 illustrates the backside of the absorbent pad 10 wherein the waste bag 18 is extended from the absorbent pad and as noted, remains attached along a border portion 20. More preferably, the bottom of the waste bag may preferably be attached at any location along the border and inward a distance of up to 4.0 inches into the absorbent pad as shown by line 21 in FIG. 5.

Figure 6:
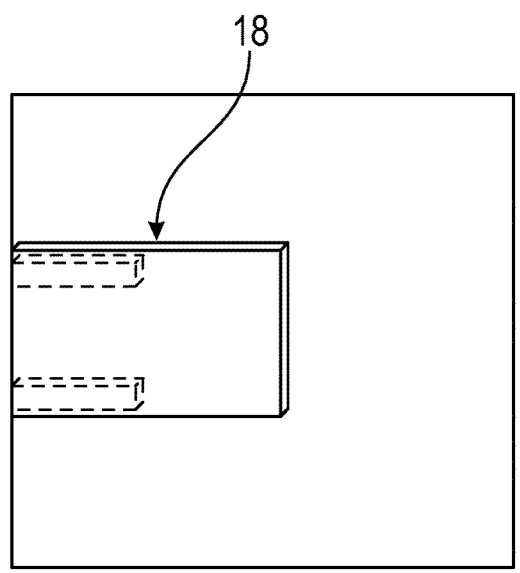
FIG. 6 shows another schematic bottom view of an example of the absorbent pad of FIG. 4, wherein the waste bag is coupled to the absorbent pad at an attachment region, consistent with embodiments of the present disclosure.
Figure 7:
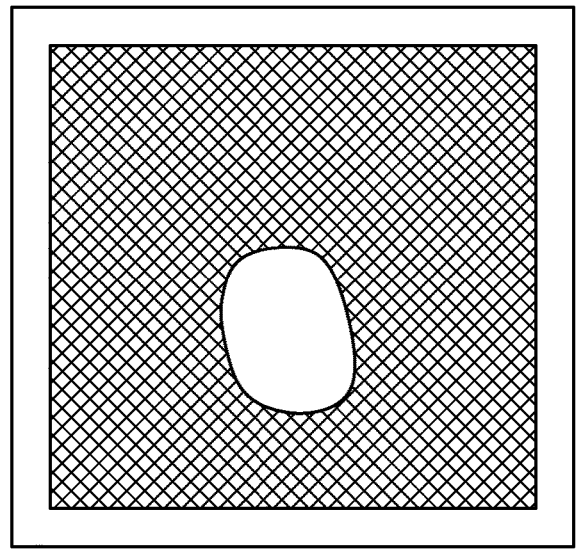
FIG. 7 shows a top view of an example of the absorbent pad of FIG. 1, wherein the absorbent pad has been soiled, consistent with embodiments of the present disclosure.
Figure 8:
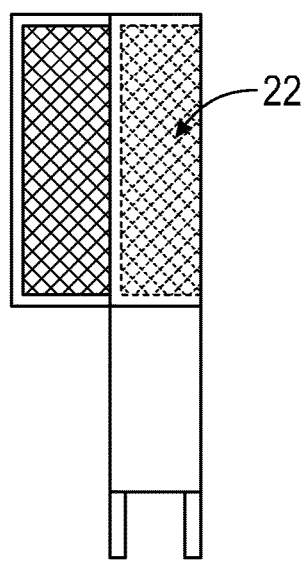
FIG. 8 shows a top view of the absorbent pad of FIG. 7, wherein a first side portion has been folded over the soiled region, consistent with embodiments of the present disclosure.
Figure 9:
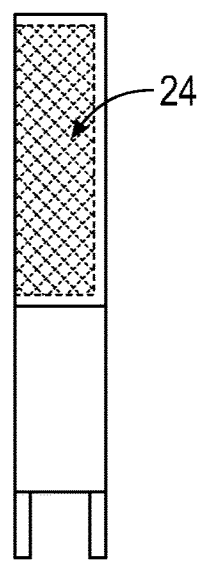
FIG. 9 shows a top view of the absorbent pad of FIG. 8, wherein a second side portion has been folded over the first side portion and the soiled region, consistent with embodiments of the present disclosure.

As may now be appreciated, the absorbent pad 10, when utilized, is initially placed on a surface where the above referenced top sheet layer, attractant layer, SAP layer, pulp layer and tissue layer are facing up and the polyolefin film layer, along with the laminated waste bag, is in contact with the floor or other selected supporting surface. As illustrated in FIG. 6, preferably, when utilized, the bag 18 is positioned on the back of the pad so that when the absorbent pad is positioned with the absorbent region 14 face-up, the bag 18 avoids from itself being soiled when the absorbent pad is utilized by the animal. Upon soiling of the absorbent pad (FIG. 7) the user may then fold one side portion (e.g., a right portion) 22 over the soiled region (FIG. 8) followed by folding of a second side portion (e.g., a left portion) 24 (FIG. 9).

Figure 10:
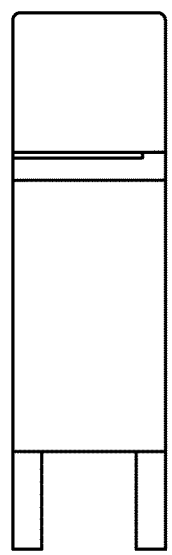
FIG. 10 shows a top view of the absorbent pad of FIG. 9 after being rolled to form a roll, consistent with embodiments of the present disclosure.
Figure 11:
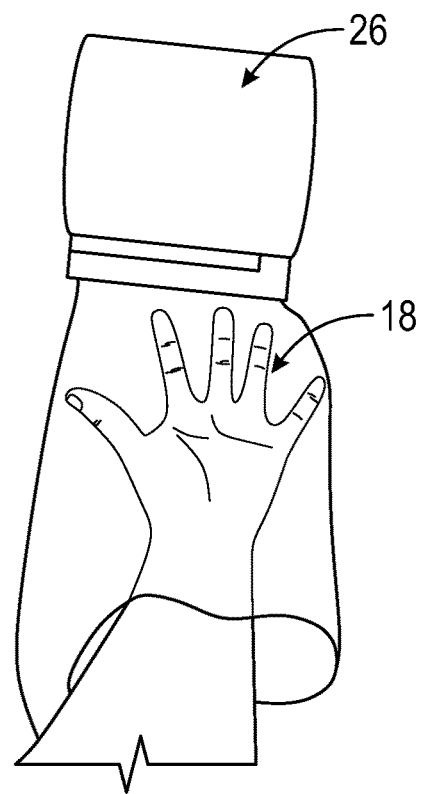
FIG. 11 shows a top perspective view of the absorbent pad of FIG. 10, wherein a user's hand is positioned within a hand cavity defined by the waste bag such that the user may invert the bag while grasping the roll to define a cavity to receive the roll, consistent with embodiments of the present disclosure.
Figure 12:
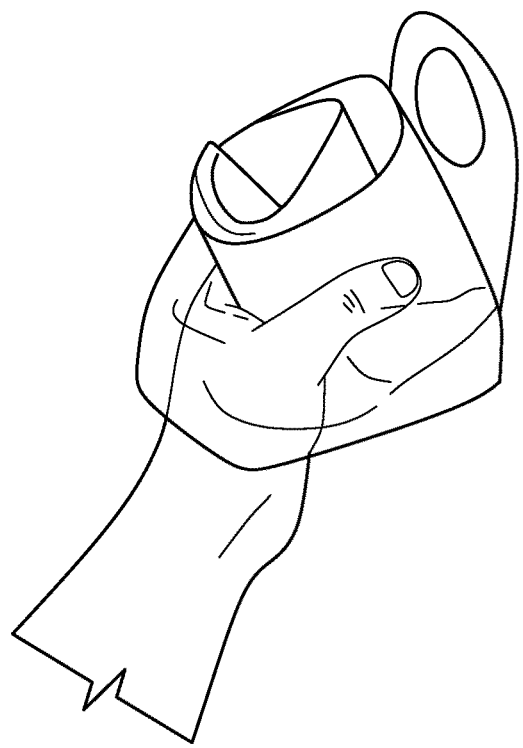
FIG. 12 shows a top perspective view of the absorbent pad of FIG. 11, wherein the user has at least partially inverted the bag while grasping the roll, consistent with embodiments of the present disclosure.
Figure 13:
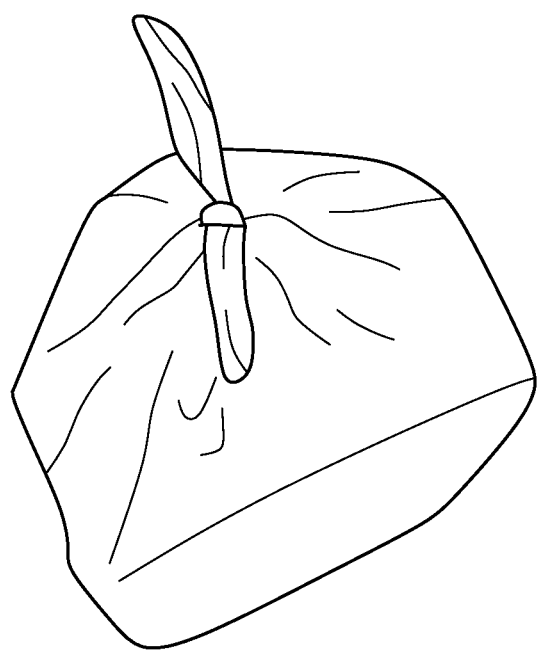
FIG. 13 shows a top perspective view of the absorbent pad of FIG. 12 after the roll has been disposed within the cavity defined by the waste bag after the waste bag has been inverted, consistent with embodiments of the present disclosure.

The user may then roll the absorbent pad towards the waste bag as shown in FIG. 10. As shown in FIG. 11, the rolled absorbent pad 26 is now in position whereby the user may insert their hand into the waste bag 18 and reach for the rolled absorbent pad 26. Upon engagement the user may then pull the rolled absorbent pad 26 into the waste bag such that the waste bag then will invert and, as shown in FIG. 13, be contained within the waste bag for convenient disposal. In addition, as illustrated in FIG. 13, preferably, the two handles can be tied to better contain and seal the soiled absorbent pad inside of the waste bag to minimize odor and exposure of its contents.

Figure 14:
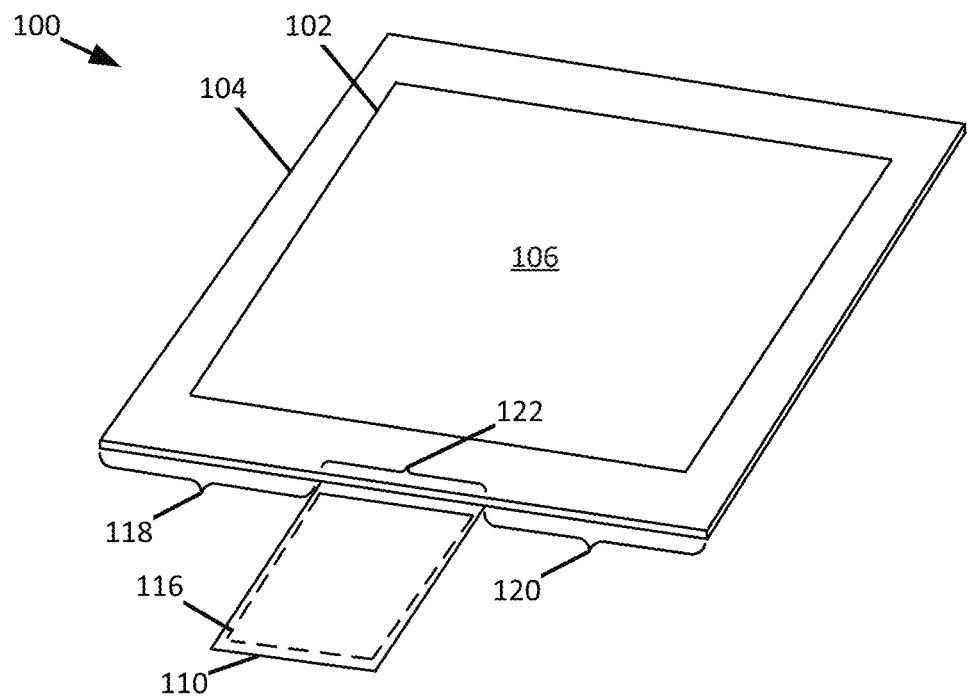
FIG. 14 shows a top perspective view of an example of an absorbent pad having a flexible bag in a use position, consistent with embodiments of the present disclosure.
Figure 15:
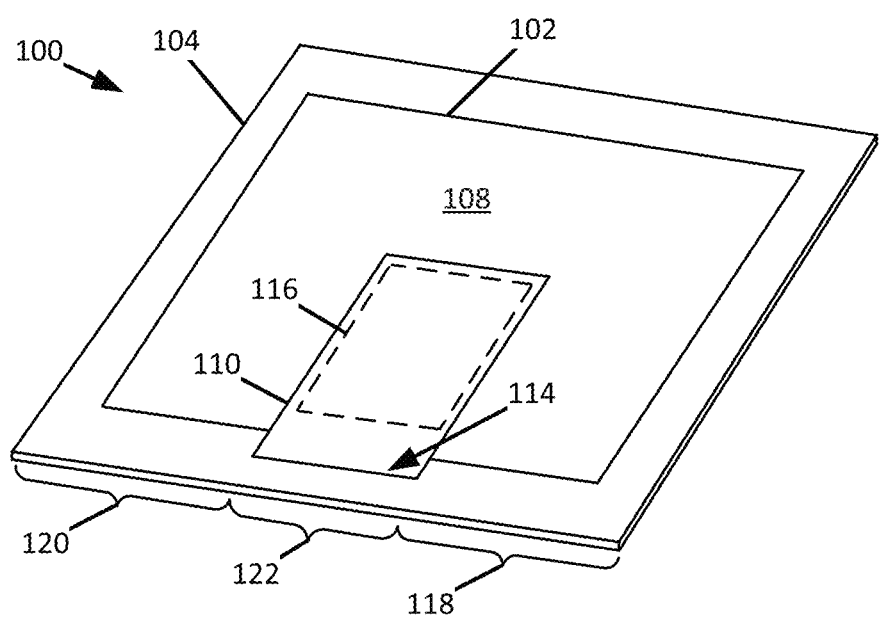
FIG. 15 shows a bottom perspective view of the absorbent pad of FIG. 14 having the flexible bag in a storage position, consistent with embodiments of the present disclosure.

FIGS. 14 and 15 show a schematic example of an absorbent pad 100, which may be another example of the absorbent pad 10 of FIG. 1. As shown, the absorbent pad 100 includes an absorbent region 102 and a border region 104 extending around the absorbent region 102. The absorbent region 102 includes a top surface 106 configured to receive animal waste and a bottom surface 108 opposite the top surface 106. A flexible bag 110 is coupled to the border region 104 at an attachment region 114. The flexible bag 110 is configured to transition between a storage position (see, e.g., FIG. 15) and a use position (see, e.g., FIG. 14) in response to pivotal movement of the flexible bag 110 about the attachment region 114. The flexible bag 110 can be coupled to the border region 104 using a lamination process, one or more adhesives, mechanical couplings, and/or any other form of coupling.

When the flexible bag 110 is in the storage position, the flexible bag 110 extends substantially parallel to the bottom surface 108 of the absorbent region 102 such that at least a portion of the bottom surface 108 is disposed between the top surface 106 of the absorbent region 102 and at least a portion of the flexible bag 110. When the flexible bag 110 is in the use position, the flexible bag 110 extends in a direction away from the absorbent region 102. When in the use position, the flexible bag 110 is further configured to receive at least a portion of the absorbent region 102 and at least a portion of the border region 104 within a cavity 116 of the flexible bag 110. The cavity 116 may be defined by one of an outer surface or an inner surface of the flexible bag 110. For example, the flexible bag 110 can be configured to be inverted such that the cavity 116 is defined by the outer surface of the flexible bag 110.

The absorbent region 102 and border region 104 can be generally described as collectively defining a left portion 118 of the absorbent pad 100, a right portion 120 of the absorbent pad 100, and a center portion 122 of the absorbent pad 100, wherein the center portion 122 extends between the left and right portions 118 and 120. The center portion 122 can include the attachment region 114 such that the flexible bag 110 extends within the center portion 122 when in the storage position.

Figure 16:
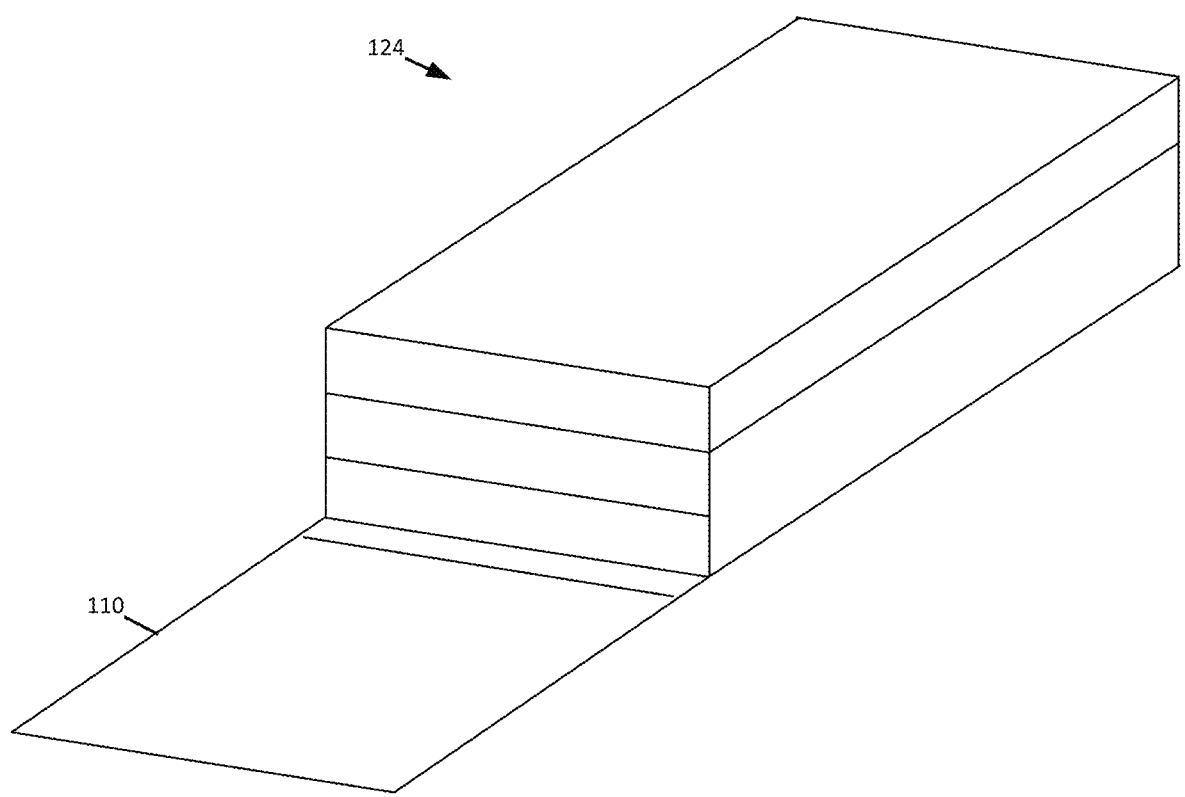
FIG. 16 shows schematic perspective view of the absorbent pad of FIG. 14, wherein a left and right portion have been folded over a center portion to form a stacked portion, consistent with embodiments of the present disclosure.

The left and right portions 118 and 120 of the absorbent pad 100 are configured to be folded towards the center portion 122 to form a stacked portion 124 (see, e.g., FIG. 16). For example, the absorbent pad 100 may include embossed regions extending on opposing sides of the center portion 122 and extending for a whole length of at least the absorbent region 102. The embossed regions may facilitate folding of the left and right portions 118 and 120 to form the stacked portion.

Figure 17:
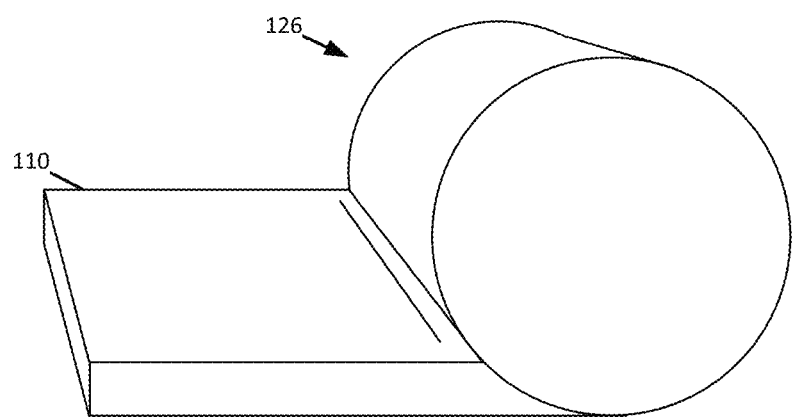
FIG. 17 shows a schematic perspective view of the absorbent pad of FIG. 16, wherein the stacked portion has been rolled to form a roll, consistent with embodiments of the present disclosure.

The stacked portion 124 can be configured to be rolled such that a roll 126 (see, e.g., FIG. 17) is formed. For example, the stacked portion 124 may be rolled in a direction of the flexible bag 110 such that the roll 126 can be received within the cavity 116 defined by the flexible bag 110.

Figure 18:
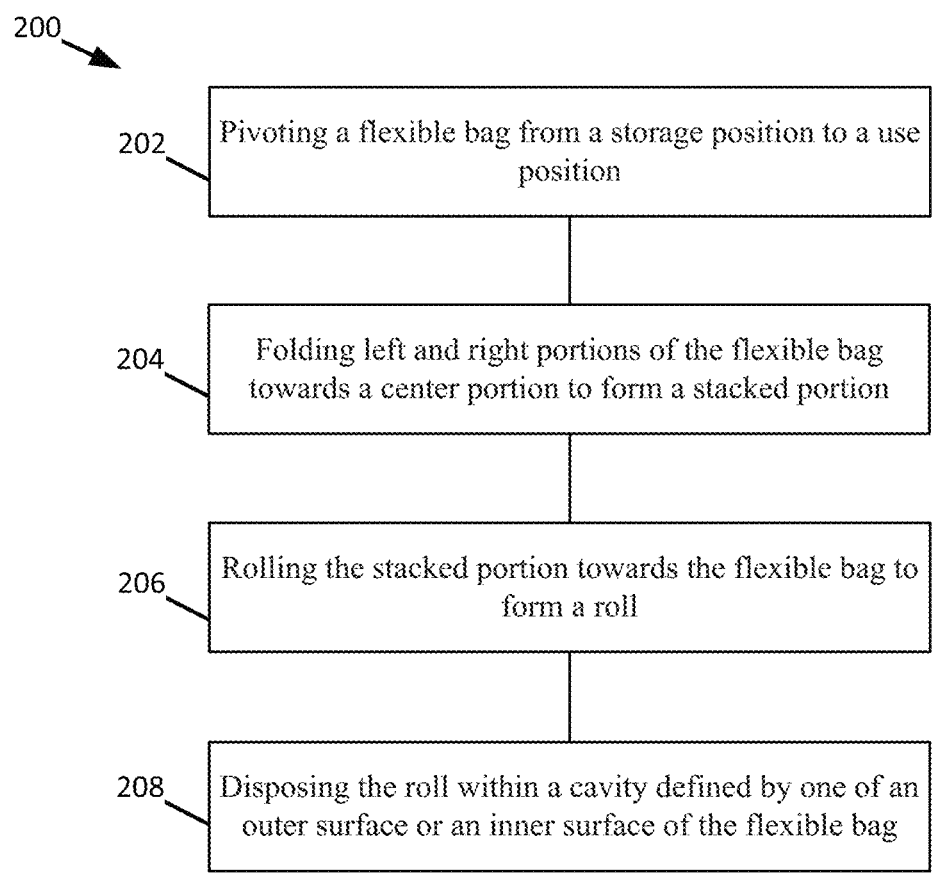
FIG. 18 shows a flow chart of a method for disposing of an absorbent pad, consistent with embodiments of the present disclosure.

FIG. 18 shows a flow chart of an example of a method 200 of disposing of an absorbent pad having a left portion, a right portion, and a center portion extending between the left and right portions, wherein a flexible bag is pivotally coupled to the center portion such that the flexible bag can be transitioned from a storage position to a use position.

The method may include a step 202. The step 202 may include pivoting the flexible bag from the storage position to the use position such that at least a portion of the flexible bag extends from the absorbent pad.

The method may include a step 204. The step 204 may include folding the left and right portions towards the center portion to form a stacked portion.

The method may include a step 206. The step 206 may include rolling the stacked portion towards the flexible bag to form a roll.

The method may include a step 208. The step 208 may include disposing the roll within a cavity defined by one of an outer surface or an inner surface of the flexible bag. In some instances, the cavity may be formed by inverting the flexible bag such that the cavity is defined by the outer surface of the flexible bag.

Figure 19:
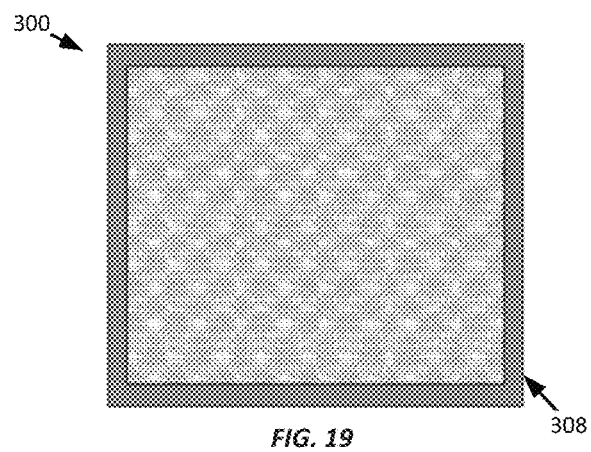
FIG. 19 shows a schematic top view of an example of an absorbent pad, consistent with embodiments of the present disclosure.
Figure 20:
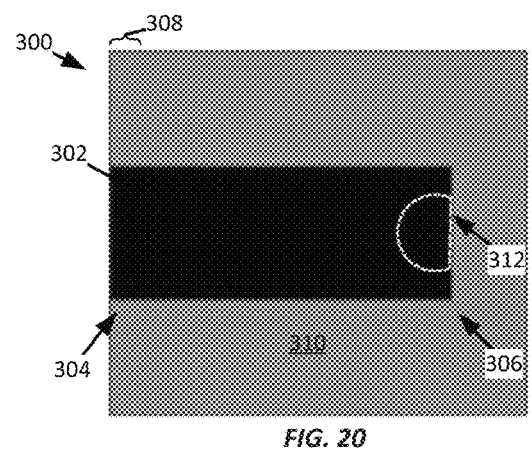
FIG. 20 shows a schematic bottom view of the absorbent pad of FIG. 19 having a flexible bag in a storage position, consistent with embodiments of the present disclosure.
Figure 21:
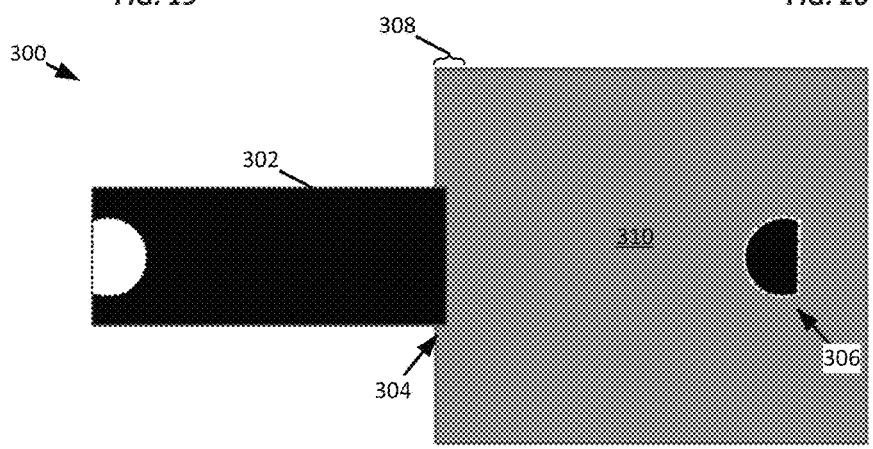
FIG. 21 shows a schematic bottom view of the absorbent pad of FIG. 20 having the flexible bag in a use position, consistent with embodiments of the present disclosure.

FIG. 19 shows a schematic top view of an absorbent pad 300, which may be another example of the absorbent pad 10 of FIG. 1. FIG. 20 shows a schematic bottom view of the absorbent pad 300 having a flexible bag 302 in a storage position and FIG. 21 shows a schematic bottom view of the absorbent pad 300 having the flexible bag 302 in a use position. As shown, when in the storage position, the flexible bag 302 may be coupled to the absorbent pad 300 at a first attachment region 304 and a second attachment region 306.

The first attachment region 304 may be located within a border region 308 of the absorbent pad 300 and the second attachment region 306 may be located on a bottom surface 310 of the absorbent pad 300 and at a location that is spaced apart from the first attachment region 304. The flexible bag 302 may include a perforated region 312 at a location between the first and second attachment regions 304 and 306. The perforated region 312 is configured such that the flexible bag 302 can be torn along the perforated region 312, allowing the flexible bag 302 to be transitioned towards the use position.

Accordingly, in broad context, the present disclosure relates to a disposable absorbent pad that is combined with a moisture impermeable bag for ready disposal, and which minimizes or eliminates the need of the user to directly contact the absorbent pad, once it is in a soiled condition. Disposal is accomplished by reaching into the moisture impermeable bag, that is preferably attached along its bottom portion to an edge of the absorbent pad, and pulling a rolled form of the absorbent pad into waste bag, which inverts to contain the soiled absorbent for disposal. The waste bag also preferably includes handles or some other sealing structure that allows the user to seal the soiled absorbent pad therein for disposal.

While the present disclosure has been described in detail for the preferred embodiments described above, it will be understood that modifications can be made without departing from the scope of the disclosure herein.

What is claimed is:

1. An absorbent floor pad to receive pet waste comprising:
   the absorbent floor pad having a planar configuration disposable on a floor to receive the pet waste when the planar configuration is disposed on the floor;
   an absorbent region having a top surface and a bottom surface, the top surface being configured such that the animal waste is receivable on the top surface and the bottom surface being opposite the top surface;
   a border region extending around the absorbent region; and
   a flexible bag coupled to the border region at an attachment region, the flexible bag having an outer surface and an inner surface and the flexible bag being configured such that the flexible bag is transitionable from a storage position to a use position in response to a pivotal movement of the flexible bag about the attachment region, wherein:
      when the flexible bag is in the storage position, the flexible bag is planar and extends substantially parallel to the bottom surface of the absorbent region such that at least a portion of the bottom surface of the absorbent region is disposed between the top surface of the absorbent region and at least a portion of the flexible bag; and
      when the flexible bag is in the use position the flexible bag is planar and extends from the border region in a direction away from the absorbent region and the flexible bag is configured such that at least a portion of the absorbent region and the border region is receivable within a cavity defined by the flexible bag, the cavity being defined by one of the flexible bag outer surface or the flexible bag inner surface; and
      when the flexible bag is in the use position, the flexible bag extends from the border region in the direction away from the absorbent region such the cavity is lateral of the absorbent region, and the cavity defined by the flexible bag is defined independent of the absorbent region and the border region.

2. The absorbent floor pad of claim 1, wherein the absorbent region and border region collectively define a left portion of the absorbent pad, a right portion of the absorbent pad, and a center portion of the absorbent pad, the center portion extending between the left and right portions and including the attachment region.

3. The absorbent floor pad of claim 2, wherein the left and right portions are foldable toward the center portion to form a stacked portion.

4. The absorbent floor pad of claim 3, wherein the stacked portion is rollable in a direction of the flexible bag to form a roll.

5. The absorbent floor pad of claim 4, wherein, when the flexible bag is in the use position, the cavity of the flexible bag is configured such that the rollis receivable within the cavity defined by the flexible bag.

6. The absorbent floor pad of claim 5, wherein, the cavity is formed by inverting the flexible bag such that the cavity is defined by the flexible bag outer surface.

7. The absorbent floor pad of claim 1, wherein the absorbent region includes a super absorbent polymer layer.

8. The absorbent floor pad of claim 7, wherein the absorbent region includes a liquid impermeable layer.

9. The absorbent floor pad of claim 8, wherein the absorbent region includes a pulp layer.

10. The absorbent floor pad of claim 9, wherein the absorbent region includes a tissue layer.

11. The absorbent floor pad of claim 10, wherein the absorbent region includes an attractant layer.

12. The absorbent floor pad of claim 11, wherein the absorbent region includes a liquid permeable top layer.

13. The absorbent floor pad of claim 12, wherein the attractant layer, the super absorbent polymer layer, the pulp layer, and the tissue layer are disposed between the liquid impermeable layer and the liquid permeable top layer.

14. The absorbent floor pad of claim 13, wherein at least a portion of the liquid impermeable layer is disposed between at least a portion of the flexible bag and at least a portion of the liquid permeable top layer when flexible bag is in the storage position.

15. The absorbent floor pad of claim 1, further comprising an indicator configured to indicate a presence of the flexible bag.

16. The absorbent floor pad of claim 1, wherein the flexible bag is coupled to the border region with a lamination.

17. The absorbent floor pad of claim 16, wherein the lamination comprises a heat sealed lamination.

18. An absorbent floor pad to receive pet waste comprising:

the absorbent floor pad having a planar configuration disposable on a floor to receive the pet waste when the planar configuration is disposed on the floor;

an absorbent region having a top surface and a bottom surface, the top surface being configured such that the pet waste is receivable on the top surface and the bottom surface being opposite the top surface, wherein the absorbent region includes:
an attractant layer;
a super absorbent polymer layer;
a liquid impermeable layer;
a pulp layer;
a tissue layer; and
a liquid permeable top layer, wherein the attractant layer, the super absorbent polymer layer, the pulp layer, and the tissue layer are disposed between the liquid impermeable layer and the liquid permeable top layer;

a border region extending around the absorbent region, wherein:
the absorbent region and border region collectively define a left portion of the absorbent pad, a right portion of the absorbent pad, and a center portion of the absorbent pad, the center portion extending between the left and right portions and including an attachment region;
the left and right portions are foldable toward the center portion to form a stacked portion; and
the stacked portion is rollable to form a roll;

a flexible bag coupled to the border region at the attachment region, the flexible bag having an outer surface and an inner surface and the flexible bag being configured such that the flexible bag is transitionable from a storage position to a use position in response to a pivotal movement of the flexible bag about the attachment region, wherein:
when the flexible bag is in the storage position, the flexible bag is planar and extends substantially parallel to the bottom surface of the absorbent region such that at least a portion of the bottom surface of the absorbent region is disposed between the top surface of the absorbent region and at least a portion of the flexible bag; and
when the flexible bag is in the use position the flexible bag is planar and extends from the border region in a direction away from the absorbent region and the flexible bag is configured to receive the roll within a cavity defined by the flexible bag, the cavity being defined by one of the flexible bag outer surface or the flexible bag inner surface; and
when the flexible bag is in the use position, the flexible bag extends from the border region in the direction away from the absorbent region such the cavity is lateral of the absorbent region, and the cavity defined by the flexible bag is defined independent of the absorbent region and the border region; and an indicator configured to indicate a presence of the flexible bag.

* * * * *